United States Patent [19]
Van Keuren

[11] Patent Number: 5,320,615
[45] Date of Patent: Jun. 14, 1994

[54] PORTABLE EMERGENCY EYE FLUSH DEVICE

[75] Inventor: Steven Van Keuren, League City, Tex.

[73] Assignee: Grumman Aerospace Corporation, Long Island, N.Y.

[21] Appl. No.: 940,331

[22] Filed: Sep. 3, 1992

[51] Int. Cl.$^5$ .............................................. A61M 35/00
[52] U.S. Cl. .................... 604/297; 604/294; 604/300
[58] Field of Search .................. 604/294–302

[56] References Cited

U.S. PATENT DOCUMENTS

| 2,101,628 | 12/1937 | Padelford | 604/294 X |
| 4,012,798 | 3/1977 | Liautaud | 604/294 X |
| 4,111,200 | 9/1978 | Sbarra et al. | 604/298 |
| 4,232,671 | 11/1980 | Crump | 604/294 |
| 4,493,119 | 1/1985 | Baumann | 604/296 X |
| 4,641,384 | 2/1987 | Landsberger | 604/295 X |
| 4,784,652 | 11/1988 | Wikström | 604/294 X |
| 4,863,443 | 9/1989 | Hornung | 604/294 X |
| 5,030,214 | 7/1991 | Spector | 604/294 X |
| 5,163,929 | 11/1992 | Py | 604/294 X |
| 5,178,613 | 1/1993 | Gibilisco | 604/294 |

FOREIGN PATENT DOCUMENTS

| 0213288 | 9/1909 | Fed. Rep. of Germany | 604/297 |
| 0457978 | 9/1913 | France | 604/297 |
| 0539416 | 6/1922 | France | 604/297 |
| 0939019 | 6/1982 | U.S.S.R. | 604/294 |

Primary Examiner—Randall L. Green
Assistant Examiner—Elizabeth M. Burke
Attorney, Agent, or Firm—Bacon & Thomas

[57] ABSTRACT

A portable eyeflushing device is disclosed having bladders which store an eyeflushing fluid. The bladders are attached to a mask that may be easily placed on a user so as to cover or enclose the user's eyes. A strap on the mask attaches the device to the user's head such that it is retained in position without the necessity of holding it in position. The bladders have tear strips on a portion extending internally of the mask which are connected to pull cords extending to the exterior of the mask and which may be manually grasped and pulled to tear the strips away from the bladder. This opens the bladders and allows the eyeflushing fluid to be dispensed from the bladders into the interior of the mask and into the user's eye. A nose piece on the interior of the mask prevents eyeflushing fluid on one side of the mask from passing to the other side of the mask and thereby prevents contamination of the user's other eye. A pair of digit covers extend outwardly from the sides of the mask. The digit covers are formed of a flexible material and may be everted into the interior of the mask to enable either the user, or an assistant to insert the thumb and forefinger into the interior of the mask and hold the eyelid open during the flushing process. The invention also has a containment bag which is attached to the mask and, prior to use, partially covers the bladders to act as a protection for the bladders. After the eyeflushing device has been used, the containment bag may be everted over the mask and closed to prevent escape of the contaminated eyeflushing fluid.

57 Claims, 6 Drawing Sheets

PORTABLE EMERGENCY EYE FLUSH DEVICE

BACKGROUND OF THE INVENTION

The present invention relates to a device for storing and supplying an eyeflushing fluid.

It is oftentimes necessary for a person to perform tasks under hazardous conditions, or to perform tasks with hazardous materials. Such tasks and materials present obvious dangers to the person despite the use of protective clothing and gear. It is often difficult to adequately protect the person's eyes and still maintain the visual acuity necessary to perform the tasks or to utilize the materials.

Despite the presence of eye protective devices, such as safety glasses, goggles, etc., it is difficult, if not impossible, to completely enclose the person's eyes in order to prevent contamination by dust, dirt, etc., especially when the necessary tasks involve the use of chemicals. Chemicals may often generate harmful gases that are not prevented from contacting the user's eye, even when wearing normal eye safety devices.

Since the person performing the task or utilizing the hazardous materials cannot be assured of 100% protection, systems have been devised to apply a flushing solution to the eye of the person in order to flush out the dust or dirt, or to neutralize eye contamination from a chemical material. While such devices have been generally successful, they have proven unduly complex, thereby limiting their portability and limiting their capability of being utilized quickly under emergency conditions.

In a zero gravity environment, such as on a manned spacecraft, an efficient, readily portable and easily useable eyeflushing device is also desirable to rapidly treat the eyes of astronauts or other occupants of the spacecraft who may be conducting experiments utilizing hazardous materials or in the event that any other contamination reaches their eyes. While many eyeflushing devices are commercially available, most if not all of them do not collect or contain the eyeflushing fluid after it has been used to flush a person's eyes. In a zero gravity spacecraft environment, it is particularly important that all eyeflushing fluid be self-contained both before and after its use.

Portable eyeflushing devices which prevent serious injury in areas remote from water supply are also necessary for use by persons engaged or employed in mining operations, expansive chemical plants, fire fighting and transferring and transporting hazardous materials. These portable eyeflush devices serve as temporary treatment until the victim can be safely transported to a first aid site, where access is available to an ANSI Z358.1 standard (15 minute/0.4 GPM minimum) eyewash supply station.

SUMMARY OF THE INVENTION

A portable eyeflushing device is disclosed having bladders which store an eyeflushing fluid. The bladders are attached to a mask that may be easily placed on a user so as to cover or enclose the user's eyes. A strap on the mask attaches the device to the user's head such that it is retained in position without the necessity of holding it in position. The bladders have tear strips on a portion extending internally of the mask which are connected to pull cords extending to the exterior of the mask and which may be manually grasped and pulled to tear the strips away from the bladder. This opens the bladders and allows the eyeflushing fluid to be dispensed from the bladders into the interior of the mask and into the user's eye. A nose piece on the interior of the mask prevents eyeflushing fluid on one side of the mask from passing to the other side of the mask and thereby prevents contamination of the user's other eye.

A pair of digit covers extend outwardly from the sides of the mask. The digit covers are formed of a flexible material and may be everted into the interior of the mask to enable either the user, or an assistant to insert the thumb and forefinger into the interior of the mask and hold the eyelid open during the flushing process.

The portable eyeflushing device according to the invention also has a containment bag which is attached to the mask and, prior to use, partially covers the bladders to act as a protection and support for the bladders. After the eyeflushing device has been used, the containment bag may be everted over the mask and closed to prevent escape of the contaminated eyeflushing fluid.

The bladders are also of flexible material such that, when the tear strips are activated, the bladders may be manually squeezed to eject the eyeflushing fluid from the bladders into the interior of the mask. Reservoirs may also be attached to the mask and may communicate with the interior of the mask via a tube extending through the mask and connected to the reservoir. Thus, after being ejected from the bladder and flushing the eye, the eyeflushing fluid may be collected in the reservoir. Reverse flow of the fluid from the reservoir back in the mask may be prevented by a one-way valve incorporated into the tube or other suitable location.

In an alternative embodiment, a pump may be associated with each bladder in order to pump the eyeflushing fluid from the bladder into the interior of the mask once the tear strips have been activated. The pumps are battery powered and the batteries may also be attached to the eyeflushing device such that it is a self-contained portable unit. Switches located on the mask may be used to actuate the pumps. In this embodiment, the bladders are also made of flexible material to enable the manual expulsion of the eyeflushing fluid from the bladders should the pumps be inoperative.

DETAILED DESCRIPTION OF THE PREFERRED EMBODIMENTS

Figure 1:
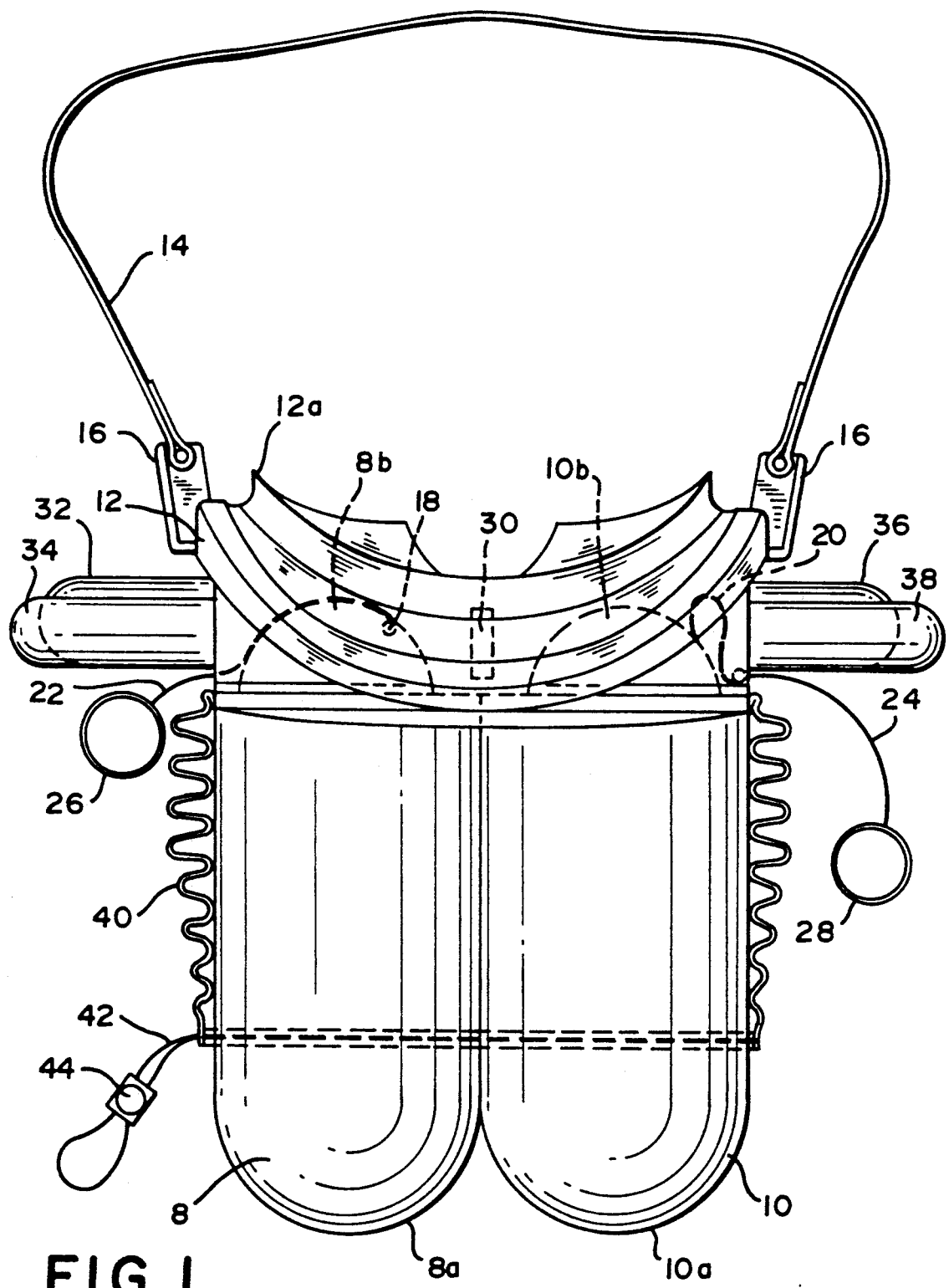
FIG. 1 is a top view of the portable eyeflushing device according to the present invention with the upper portion of the containment bag deleted for the purposes of clarity.
Figure 2:
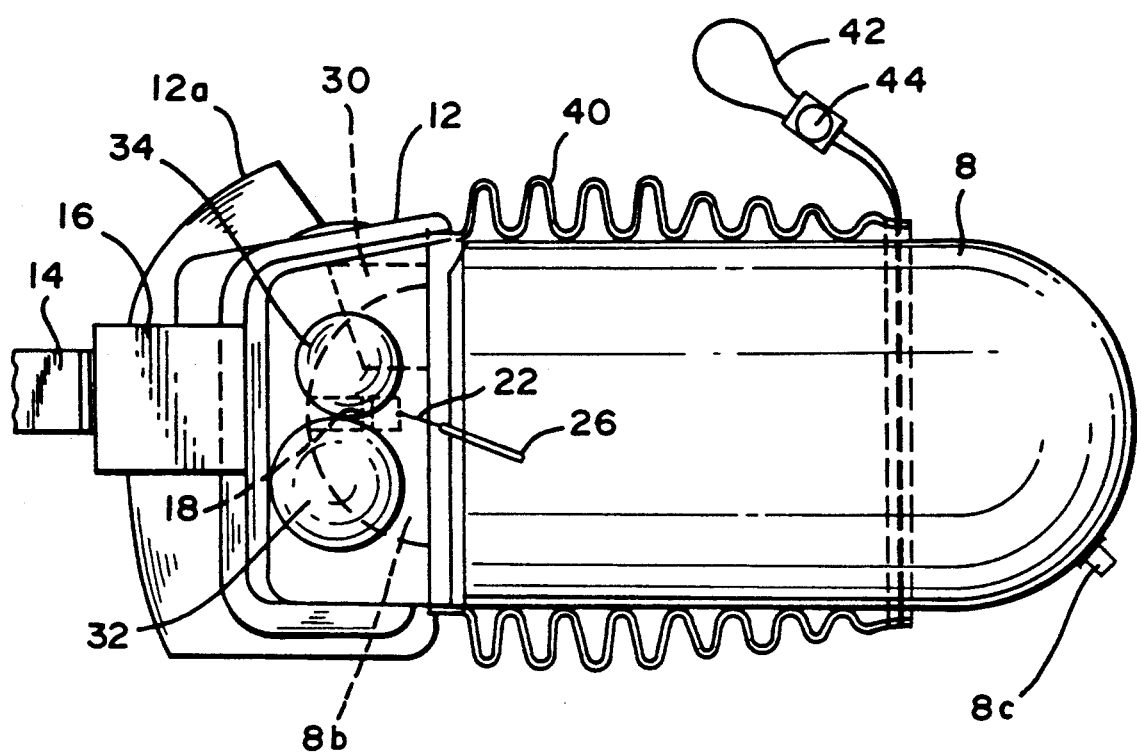
FIG. 2 is a side view of the portable eyeflushing device shown in FIG. 1 with the side of the containment bag removed for clarity.
Figure 3:
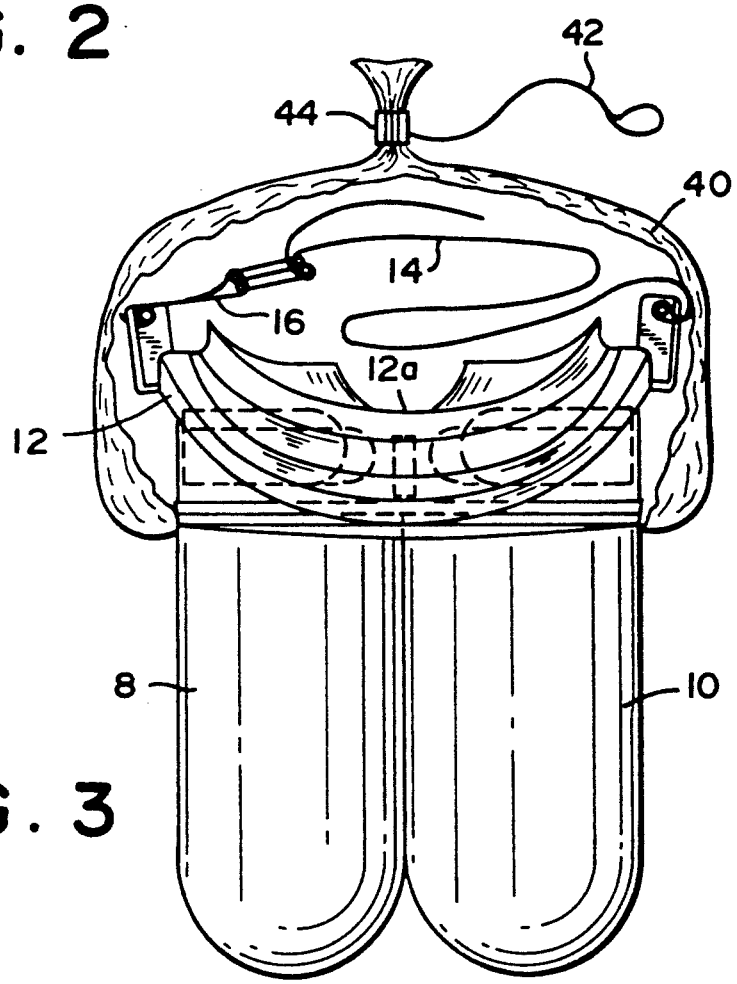
FIG. 3 is a top view of the portion eyeflushing device shown in FIGS. 1 and 2 with the containment bag deployed after the device has been used.

A first embodiment of the portable eyeflushing device according to this invention is illustrated in FIGS. 1-3. As can be seen, the device comprises bladders 8 and 10 having generally cylindrical configuration. The bladders 8 and 10 have generally hemispherical external ends 8a and 10a, and are attached to mask 12 at their opposite ends. The mask has a portion 12a adapted, in known fashion, to fit against the face of the user such that, when attached, the mask will cover the eyes of the user. A strap 14 attached to the mask 12 via brackets 16 extends around the user's head in order to hold the mask in its position covering the eyes without additional assistance from either the user or an assistant. Strap 14 may be elastic and/or may be otherwise readily adjustable in length to accommodate various users. Strap 14 may be rotated 180° to act as an additional support for bladders 8 and 10 when the eyeflush is in the stored state.

A portion 8b and 10b of each of the bladders 8 and 10 extends into the interior of the mask 12. These portions, as illustrated, may be generally hemispherical in configuration. Tear strips 18 and 20 are operatively associated with each portion 8b and 10b, respectively, to releasably seal the bladders 8 and 10. When in position of tear strip 18, in FIG. 1, the bladder (in this particular instance bladder 8) is sealed and is filled with an eyeflushing fluid. The bladders may be initially filled through bladder inlets, illustrated at 8c in FIG. 2. Pull cords 22 and 24 are affixed to the tear strips 18 and 20, respectively, and extend exteriorly of the mask 12. Rings 26 and 28 may be attached to the exterior ends of pull cords 22 and 24 to facilitate the manual actuation of the pull cords. Other forms of releasable seals other than tear strips 18 and 20 also could be utilized (e.g. weakened bladder walls and the like).

When a pull cord 22 or 24 is pulled by the user, it severs the tear strip from its respective bladder, thereby unsealing or opening the bladder and allowing its eyeflushing fluid contents to flow out of the respective bladder. The released position is illustrated by tear strip 20 in FIG. 1. It should be noted that tear strips 18 and 20 are separately and individually actuable. A partition member 30 is located on the interior of the mask so as to bear against the face and the bridge of the nose of the user in order to separate the interior of the mask 12 into separate compartments, one for each eye. This prevents contamination of one eye by the eyeflushing fluid from the bladder for the opposite eye.

A plurality of digit cover members 32, 34, 36 and 38 extend from opposite sides of the mask 12 as illustrated in FIG. 1. The digit cover members are formed of a flexible material and are attached to the sides of the mask so as to cover openings in the mask sides. The flexible material enables each of the digit cover members 32, 34, 36 and 38 to be everted from their normally outwardly extending positions to positions extending inwardly into the interior of the mask 12. The digit cover members allow either the user or an assistant to insert their forefinger and thumb into the interior of the mask so as to hold the eyelid open during the eyeflushing procedure.

A containment bag 40 has one end fixedly attached to mask 12 and, prior to the usage of the device, extends over a portion of the bladders 8 and 10. The containment bag 40 is formed of a flexible material and, in this position, may also serve as a protective cover for the flexible bladders 8 and 10. The distal end of the containment bag 40 has a drawstring 42 and a clasp 44.

As can be seen, the eyeflushing device according to the invention is readily portable owing to its relatively small size and weight enabling it to be either carried, or stowed in areas in which potential eye hazards exist.

In use, the eyeflushing device, normally in the configuration shown in FIG. 1, is placed over the face of the user such that the mask 12 covers the eye area and is held in place by strap 14. The pull cord for the eye that is contaminated is pulled, tearing away the associated tear strip and opening the respective bladder. The bladder is then squeezed manually to force the eyeflushing fluid out of the bladder, into the interior of the mask 12 and against the contaminated eye. If necessary, the user or an assistant can evert the respective digit cover members to use the finger and thumb to hold the eyelid open to overcome the reflex action to close the eye during the flushing procedure. When the eyeflushing procedure has been completed or the victum has been transported to a first aid site, the device is removed from the user's face and the containment bag is pulled up over the mask portion and sealed with the drawstring, as illustrated in FIG. 3. The containment bag prevents the escape of the contaminated eyeflushing fluid before it can be safely discarded.

Figure 4:
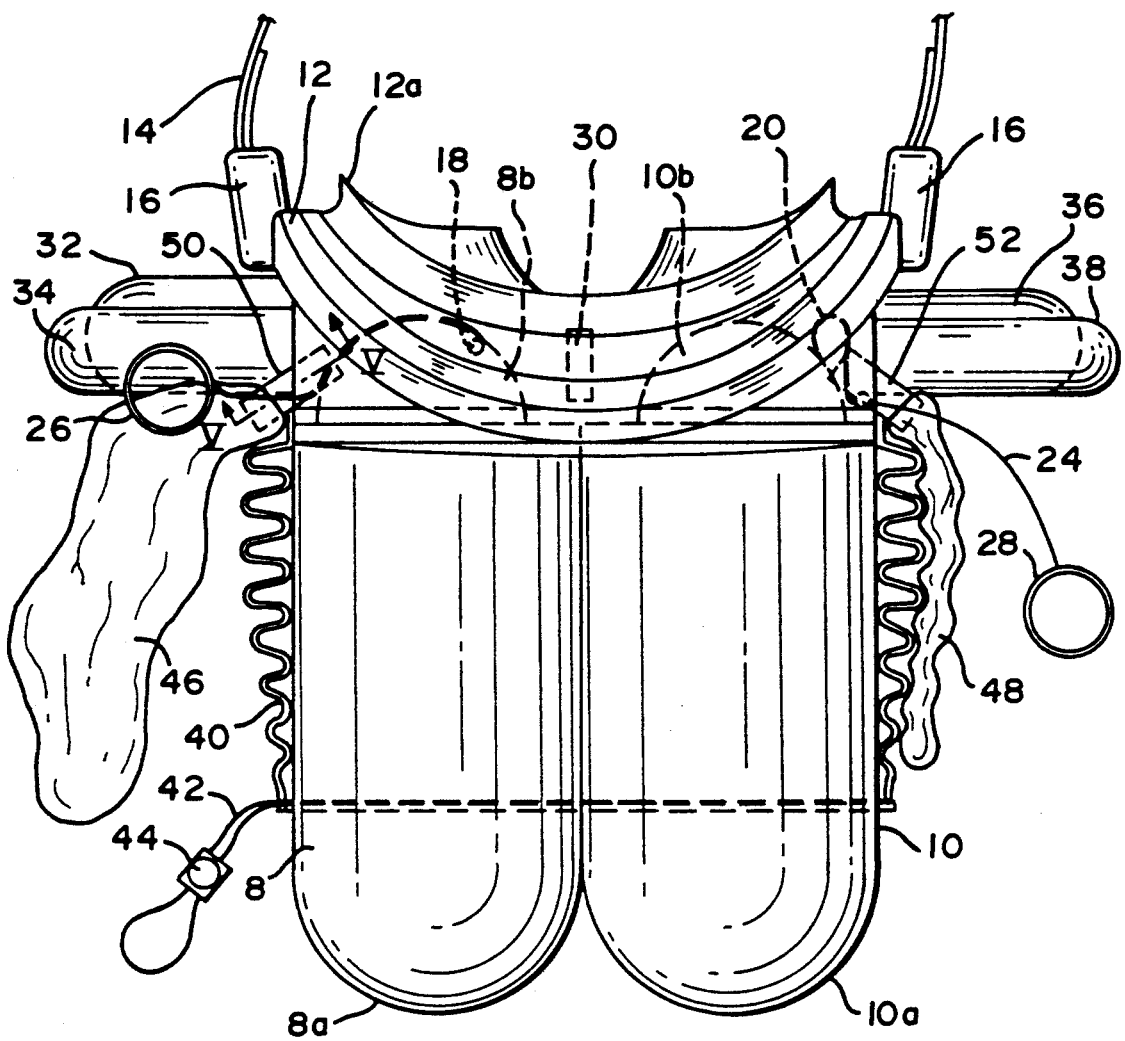
FIG. 4 is a top view a second embodiment of the portable eyeflushing device according to the invention with the upper portion of the containment bag deleted for purposes of clarity.
Figure 5:
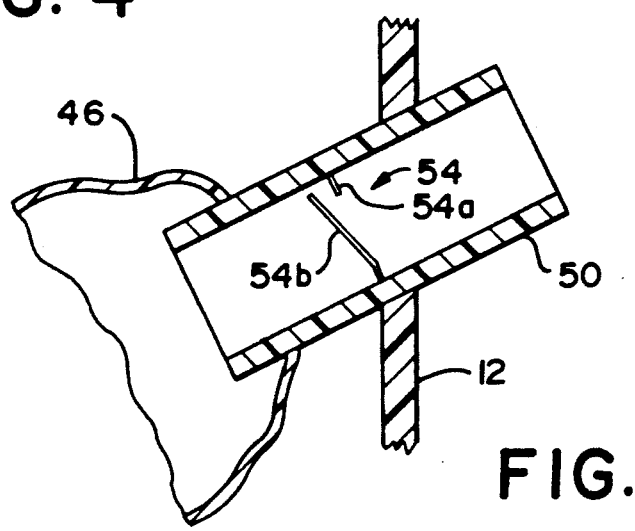
FIG. 5 is a cross-sectional view taken along Line V—V in FIG. 4.

In the alternative embodiment illustrated in FIGS. 4 and 5, reservoirs 46 and 48 are located on opposite sides of mask 12 and communicate with the interior of the mask 12 via tubes 50 and 52. The structure and function of the bladders 8 and 10, the mask 12, the evertable digit covers 32, 34, 36 and 38, as well as tear strips 18 and 20 are identical to the previously described embodiment. However, the presence of the reservoirs 46 and 48 enables the use of manual reciprocating eyeflushing techniques. As the eyeflushing fluid is forced out of one of the bladders, into the interior of the mask and against the eye, it subsequentially flows through one of the tubes 50, 52 and into one of the reservoirs 46, 48. If reciprocating eyeflushing is desired, the reservoir into which the eyeflushing fluid is displaced may be squeezed, thereby forcing the eyeflushing fluid from the reservoir, back into the interior of the mask 12.

If it is desired to prevent the return flow of the eyeflushing fluid from either of the reservoirs 46 and 48, a one-way valve 54 may be incorporated into the tubes 50 and 52. As illustrated in FIG. 5, the one-way valve 54 may comprise a valve seat 54a and a movable valve member 54b. Pressure exerted on movable valve member 54b by the eyeflushing fluid within the interior of the mask 12 displaces it from the valve seat 54a enabling the eyeflushing fluid to flow into the reservoir, in this instance reservoir 46. However, any pressure on the eyeflushing fluid within in the reservoir 46 will urge valve element 54 against the seat 54a, thereby preventing any return flow. The actual one-way valve, of course, could be of any suitable design to achieve the intended purpose.

This embodiment of the portable eyeflushing device has closed loop eyeflushing and prevents the escape of any eyeflushing fluid. This is particularly important in low or zero gravity applications of the device, since, under those circumstances, the escape of any minute particles of fluid could cause serious damage to personnel and to sensitive equipment.

As in the previous embodiment, the containment bag 40 may be everted over the mask and the reservoirs upon completion of the eyeflushing procedure and sealed with the drawstring and clasp.

Figure 6:
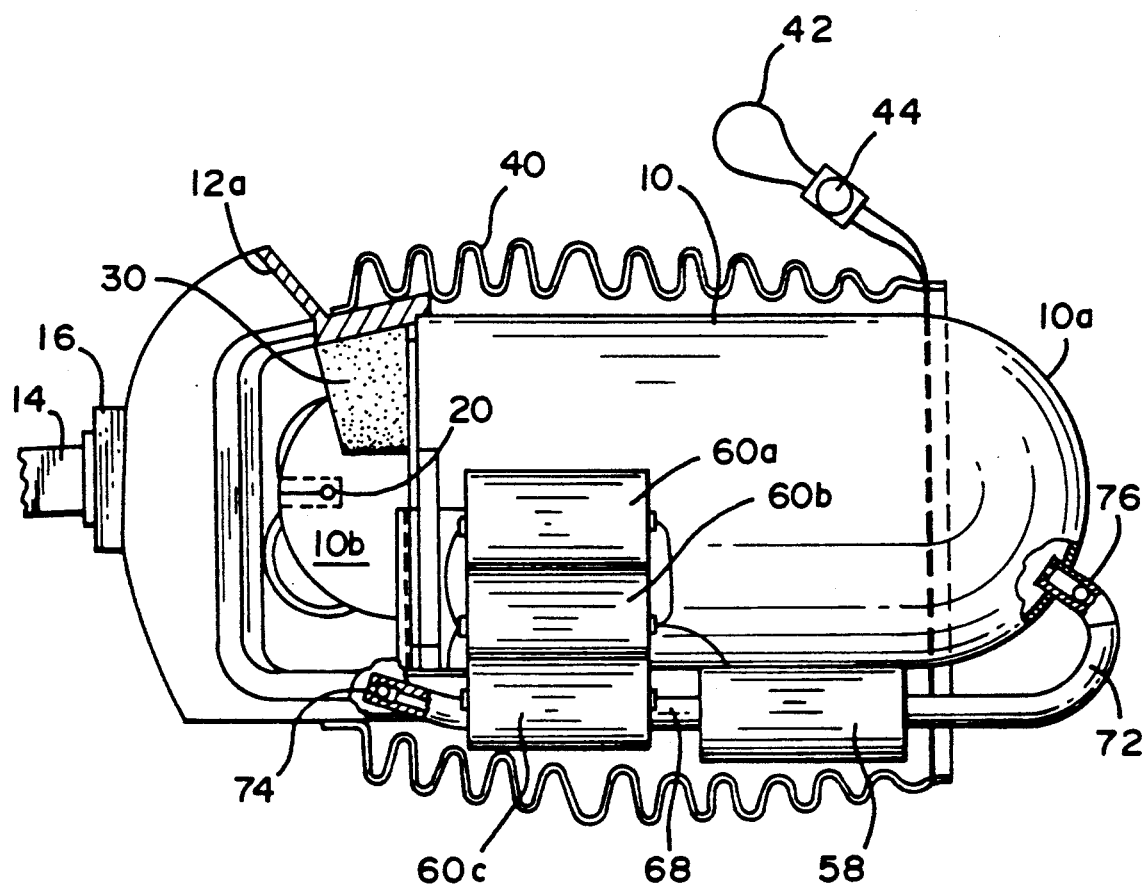
FIG. 6 is a side, cross-sectional view taken along Line VI—VI in FIG. 7 of a third embodiment of the portable eyeflushing device according to the invention.
Figure 7:
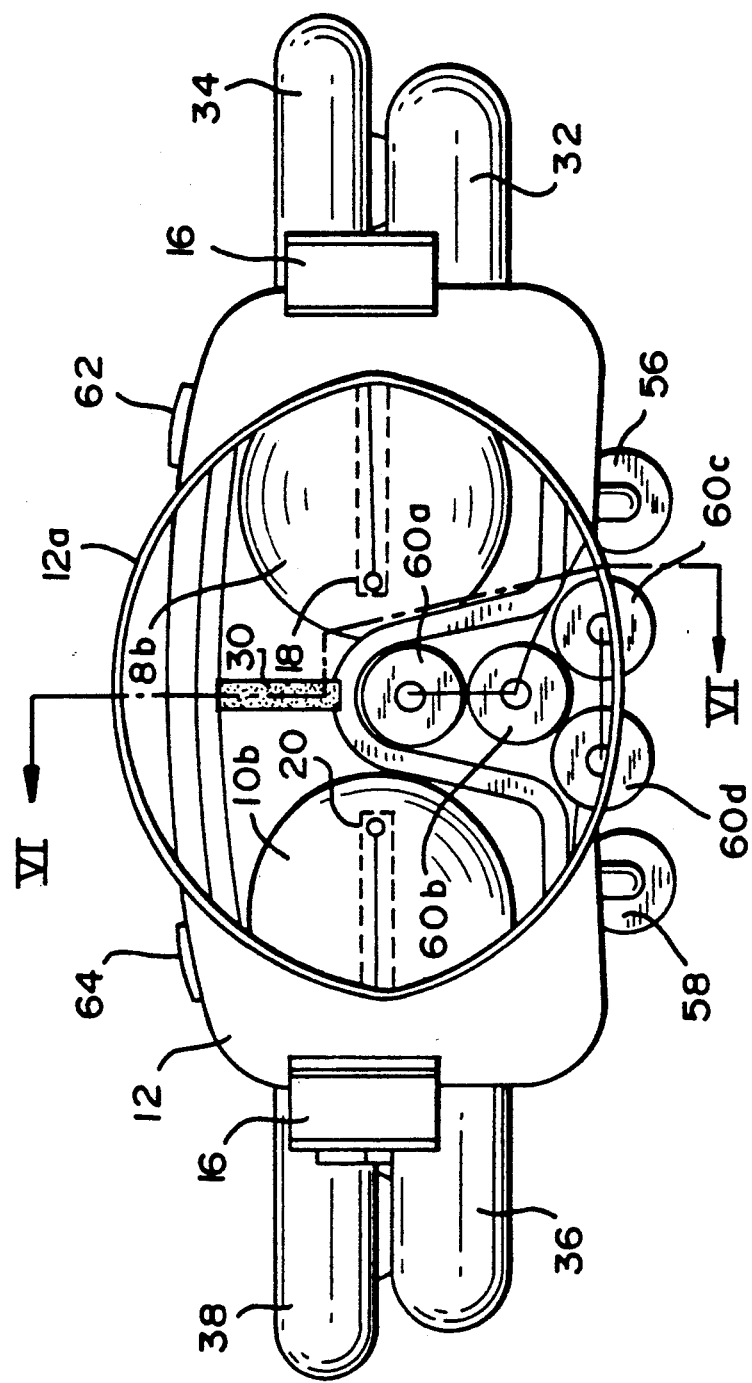
FIG. 7 is a rear view of the portable eyeflushing device illustrated in FIG. 6.
Figure 8:
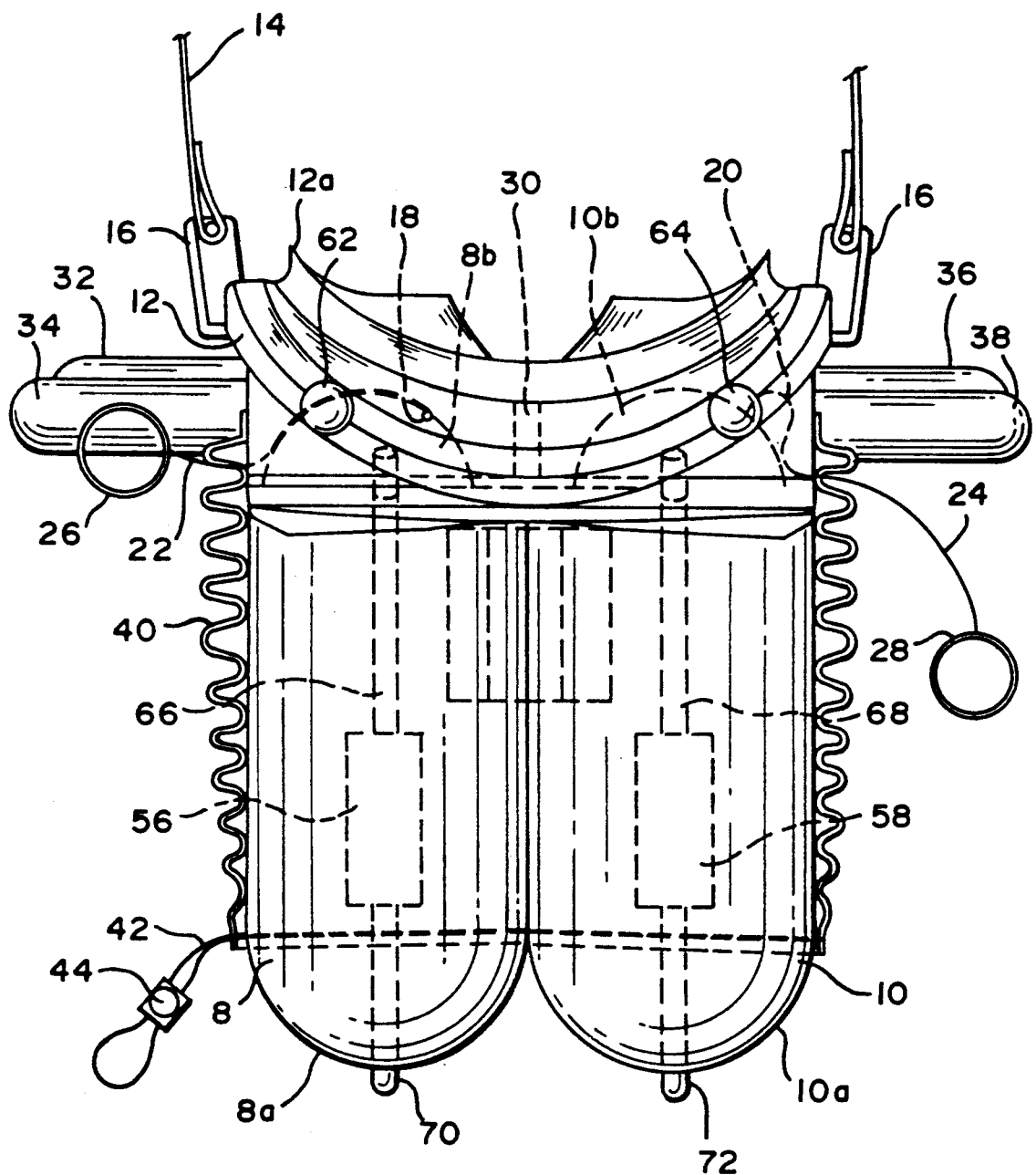
FIG. 8 is a top view of the third embodiment of the portable eyeflushing illustrated in FIGS. 6 and 7 with the top portion of the containment bag deleted for clarity.

A third embodiment of the portable eyeflushing device is illustrated in FIGS. 6–8. In this embodiment the structures and functions of the bladders 8 and 10, the mask 12, the digit cover members 32, 34, 36 and 38, the tear strips 18 and 20, as well as the containment bag 40 are the same as in the previously described embodiments. However, in this embodiment, each of the bladders 8 and 10 has a pump associated therewith. The pumps, illustrated at 56 and 58, may be any known type of pump, such as an impeller pump, without departing from the scope of this invention. The pumps are preferably battery powered and the batteries, indicated at 60a, 60b, 60c and 60d, are physically attached to the eyeflushing device so that it is completely self-contained and portable. In known fashion, the batteries 60a–60d are electrically connected to the pumps 56 and 58, as well as to operating switches 62 and 64, which may be located on an upper portion of mask 12. Switches 62 and 64 may be crush switches and, when actuated, turn on either pump 56 or 58. A recirculating flow path is set up via tubes 66 and 68, which connect the interior of the mask 12 to the pumps 56 and 58, as well as tubes 70 and 72 which connect the pumps 56 and 58, respectively, with the inlets for bladders 8 and 10. The bladder inlets are located at the point furtherest from the eye so as to maximize the return distance which achieves maximum dilution. If a one direction eye flush is desired, ball check valves may be included in tubes 66, 68, as well as tubes 70 and 72. These are schematically illustrated at 74 and 76 in FIG. 6. In the event that one or both of the pumps 56 and 58 fail to operate, the eyeflushing fluid may still be manually expelled from either of the bladders 8 and 10 as in the embodiments previously described.

It is within the scope of this invention that the bladders 8 and 10 may be removably attached to the mask 12. In this way, different bladders may be utilized with a common mask, each bladder containing the proper eyeflushing fluid to dilute the specific hazard encountered. The bladders may be color coded to insure that the proper eyeflushing fluid is utilized for a specific task or material.

The foregoing description is provided for illustrative purposes only and should not be construed as in any way limiting this invention, the scope of which is defined solely by the appended claims.

I claim:

1. A portable eyeflushing device comprising:
   a) at least one bladder to contain an eyeflushing fluid;
   b) means attached to the at least one bladder to releasably seal the at least one bladder which means, when released, allows eyeflushing fluid to escape from the at least one bladder;
   c) attaching means connected to the at least one bladder configured to attach the at least one bladder to a head of a user such that the at least one bladder is located adjacent to an eye, wherein the attaching means comprises a mask configured to fit against a face of a user so as to cover eyes of the user, the mask defining a mask interior;
   d) a containment bag connected to the mask and configured to enclose the mask; and,
   e) closure means on the containment bag such that the containment bag may be closed when enclosing the mask to prevent escape of eyeflushing fluid.

2. The portable eyeflushing device of claim 1 further comprising a compressible nose piece located on the interior of the mask and configured to bear against a portion of the face of a user thereby forming two non-communicating eye chambers, preventing cross-contamination of the eyes.

3. The portable eyeflushing device of claim 1, said attaching means further comprising a strap attached to the mask configured to fit around a head of a user.

4. The portable eyeflushing device of claim 1 wherein the mask has at least one side portion and further comprising at least one digit cover member attached to the side portion and configured to extend into the mask interior.

5. The portable eyeflushing device of claim 4 wherein the at least one digit cover member normally extends from the at least one side of the mask away from the mask interior and is formed of a flexible material such that it may be everted so as to extend into the mask interior.

6. The portable eyeflushing device of claim 4 comprising a pair of digit cover members attached to the at least one side portion and configured to extend into the mask interior.

7. The portable eyeflushing device of claim 1 wherein the releasable seal means comprises:
   a) a tear away strip connected to the at least one bladder; and,
   b) a pull cord attached to the tear away strip.

8. The portable eyeflushing device of claim 1 further comprising:
   a) a pair of bladders, each configured to contain eyeflushing fluid; and,
   b) releasable seal means attached to each bladder, which, when released, allows eyeflushing fluid to escape from the bladder into the mask interior.

9. The portable eyeflushing device of claim 1 further comprising: at least one reservoir connected to the mask to receive eyeflushing fluid.

10. The portable eyeflushing device of claim 9 flushing comprising a compressible nose piece located on the interior of the mask and configured to bear against a portion of the face of a user thereby forming two non-communicating eye chambers, preventing cross-contamination of the eyes.

11. The portable eyeflushing device of claim 9 wherein further comprising fluid communication means connecting the mask and the at least one reservoir so as to establish fluid communication between the mask interior and the at least one reservoir.

12. The portable eyeflushing device of claim 11 wherein the mask has at least one side portion and wherein the fluid communication means comprises a tube extending through the at least one side portion of the mask.

13. The portable eyeflushing device of claim 11 wherein the fluid communication means further comprises one way valve means to permit fluid flow from the mask interior into the at least one reservoir.

14. The portable eyeflushing device of claim 9, said attaching means further comprises a strap attached to the mask configured to fit around ahead of a user.

15. The portable eyeflushing device of claim 9 wherein the mask has at least one side portion and further comprising at least one digit cover member attached to the side portion and configured to extend into the mask interior.

16. The portable eyeflushing device of claim 15 wherein the at least one digit cover member normally extends from the at least one side of the mask away from the mask interior and is formed of a flexible material such that it may be everted so as to extend into the mask interior.

17. The portable eyeflushing device of claim 15 comprising a pair of digit cover members attached to the at least one side portion and configured to extend into the mask interior.

18. The portable eyeflushing device of claim 9 further comprising:
 a) a pair of reservoirs; and,
 b) fluid communication means operatively interposed between the mask and each reservoir so as to establish fluid communication between the mask interior and the pair of reservoirs.

19. The portable eyeflushing device of claim 1 further comprising: pump means connected between the at least one bladder and the mask interior so as to pump eyeflushing fluid from the at least one bladder into the mask interior.

20. The portable eyeflushing device of claim 19 further comprising a compressible nose piece located on the interior of the mask and configured to bear against a portion of the face of a user thereby forming two non-communicating eye chambers, preventing cross-contamination of the eyes.

21. The portable eyeflushing device of claim 19 wherein the pump means is electrically operated and further comprising at least one battery connected to the pump means so as to supply electrical power thereto.

22. The portable eyeflushing device of claim 19 further comprising manually actuated switch means connected to the pump means to control the pump means.

23. The portable eyeflushing device of claim 19 further comprising:
 a) a pair of bladders, each configured to contain eyeflushing fluid; and,
 b) releasable seal means attached to each bladder which, when released, allows eyeflushing fluid to escape from the bladder into the mask interior.

24. The portable eyeflushing device of claim 23 further comprising a separate pump means connected to each of the pair of bladders.

25. The portable eyeflushing device of claim 19 further comprising: at least one reservoir connected to the mask to receive eyeflushing fluid.

26. The portable eyeflushing device of claim 25 further comprising fluid communication means connecting the mask and the at least one reservoir so as to establish fluid communication between the mask interior and the at least one reservoir.

27. The portable eyeflushing device of claim 26 wherein the mask has at least one side portion and wherein the fluid communication means comprises a tube extending through the at least one side portion of the mask.

28. The portable eyeflushing device of claim 26 wherein the communication means further comprises one way valve means to permit fluid flow from the mask interior into the at least one reservoir.

29. The portable eyeflushing device of claim 25 further comprising:
 a) a pair of reservoirs; and,
 b) fluid communication means extending between the mask and each reservoir so as to establish fluid communication between the mask interior and the pair of reservoirs.

30. The portable eyeflushing device of claim 19, wherein said attaching means further comprises a strap attached to the mask configured to fit around ahead of a user.

31. The portable eyeflushing device of claim 19 wherein the mask has at least one side portion and further comprising at least one digit cover member attached to the side portion and configured to extend into the mask interior.

32. The portable eyeflushing device of claim 31 wherein the at least one digit cover member normally extends from the at least one side of the mask away from the mask interior and is formed of a flexible material such that it may be everted so as to extend into the mask interior.

33. The portable eyeflushing device of claim 32 comprising a pair of digit cover members attached to the at least one side portion and configured to extend into the mask interior.

34. A portable eyeflushing device comprising:
 a) at least one bladder to contain an eyeflushing fluid;
 b) means attached to the at least one bladder to releasably seal the at least one bladder which means, when released, allows eyeflushing fluid to escape from the at least one bladder;
 c) attaching means connected to the at least one bladder configured to attach the at least one bladder to a head of a user such that the at least one bladder is located adjacent to an eye, wherein the attaching means comprises a mask configured to fit against a face of a user so as to cover eyes of the user, the mask defining a mask interior and having at least one side portion; and
 d) at least one digit cover member attached to the at least one side portion configured to extend into the mask interior.

35. The portable eyeflushing device of claim 34 wherein the at least one digit cover member normally extends from the at least one side of the mask away from the mask interior and is formed of a flexible material such that it may be everted so as to extend into the mask interior.

36. The portable eyeflushing device of claim 34 comprising a pair of digit cover members attached to the at least one side portion and configured to extend into the mask interior.

37. A portable eyeflushing device comprising:
 a) at least one bladder to contain an eyeflushing fluid;
 b) means attached to the at least one bladder to releasably seal the at least one bladder which means, when released, allows eyeflushing fluid to escape from the at least one bladder;
 c) attaching means connected to the at least one bladder configured to attach the at least one bladder to a head of a user such that the at least one bladder is located adjacent to an eye wherein the attaching means comprises a mask configured to fit against a face of a user so as to cover eyes of the user, the mask having at least one side portion and defining a mask interior;
 d) at least one reservoir connected to the mask to receive eyeflushing fluid; and,
 e) fluid communication means connecting the mask and the at least one reservoir so as to establish fluid communication between the mask interior and the at least one reservoir, wherein the fluid communication means comprises a tube extending through the at least one side portion of the mask.

38. The portable eyeflushing device of claim 37 wherein the fluid communication means further comprises one way valve means to permit fluid flow from the mask interior into the at least one reservoir.

39. A portable eyeflushing device comprising:
a) at least one bladder to contain an eyeflushing fluid;
b) means attached to the at least one bladder to releasably seal the at least one bladder which means, when released, allows eyeflushing fluid to escape from the at least one bladder;
c) attaching means connected to the at least one bladder configured to attach the at least one bladder to a head of a user such that the at least one bladder is located adjacent to an eye wherein the attaching means comprises a mask configured to fit against a face of a user so as to cover eyes of the user, the mask defining a mask interior wherein the mask has at least one side portion and further comprising at least one digit cover member attached to the side portion and adapted to extend into the mask interior; and
d) at least one reservoir connected to the mask to receive eyeflushing fluid.

40. The portable eyeflushing device of claim 39 wherein the at least one digit cover member normally extends from the at least one side of the mask away from the mask interior and is formed of a flexible material such that it may be everted so as to extend into the mask interior.

41. The portable eyeflushing device of claim 39 comprising a pair of digit cover members attached to the at least one side portion and configured to extend into the mask interior.

42. A portable eyeflushing device comprising:
a) at least one bladder to contain an eyeflushing fluid;
b) means attached to the at least one bladder to releasably seal the at least one bladder which means, when released, allows eyeflushing fluid to escape from the at least one bladder;
c) attaching means connected to the at least one bladder configured to attach the at least one bladder to a head of a user such that the at least one bladder is located adjacent to an eye wherein the attaching means comprises a mask configured to fit against a face of a user so as to cover eyes of the user, the mask defining a mask interior; and,
d) pump means connected between the at least one bladder and the mask interior so as to pump eyeflushing fluid from the at least one bladder into the mask interior.

43. The portable eyeflushing device of claim 42 further comprising a compressible nose piece located on the interior of the mask and configured to bear against a portion of the face of a user thereby forming two non-communicating eye chambers, preventing cross-contamination of the eyes.

44. The portable eyeflushing device of claim 42 wherein the pump means is electrically operated and further comprising at least one battery connected to the pump means so as to supply electrical power thereto.

45. The portable eyeflushing device of claim 42 further comprising manually actuated switch means connected to the pump means to control the pump means.

46. The portable eyeflushing device of claim 42 further comprising:
a) a pair of bladders, each configured to contain eyeflushing fluid; and,
b) releasable seal means attached to each bladder which, when released, allows eyeflushing fluid to escape from the bladder into the mask interior.

47. The portable eyeflushing device of claim 46 further comprising a separate pump means connected to each of the pair of bladders.

48. The portable eyeflushing device of claim 42 further comprising: at least one reservoir connected to the mask to receive eyeflushing fluid after it has escaped from the at least one bladder.

49. The portable eyeflushing device of claim 48 further comprising fluid communication means connecting the mask and the at least one reservoir so as to establish fluid communication between the mask interior and the at least one reservoir.

50. The portable eyeflushing device of claim 49 wherein the mask has at least one side portion and wherein the fluid communication means comprises a tube extending through the at least one side portion of the mask.

51. The portable eyeflushing device of claim 49 wherein the communication means further comprises one way valve means to permit fluid flow from the mask interior into the at least one reservoir.

52. The portable eyeflushing device of claim 48 further comprising:
a) a pair of reservoirs; and,
b) fluid communication means extending between the mask and each reservoir so as to establish fluid communication between the mask interior and the pair of reservoirs.

53. The portable eyeflushing device of claim 42, said attaching means further comprises a strap attached to the mask configured to fit around a head of a user.

54. The portable eyeflushing device of claim 42 further comprising:
a) a containment bag connected to the mask and configured to enclose the mask; and,
b) closure means on the containment bag such that the containment bag may be closed when enclosing the mask to prevent escape of eyeflushing fluid.

55. The portable eyeflushing device of claim 42 wherein the mask has at least one side portion and further comprising at least one digit cover member attached to the side portion and configured to extend into the mask interior.

56. The portable eyeflushing device of claim 55 wherein the at least one digit cover member normally extends from the at least one side of the mask away from the mask interior and is formed of a flexible material such that it may be everted so as to extend into the mask interior.

57. The portable eyeflushing device of claim 55 comprising a pair of digit cover members attached to the at least one side portion and configured to extend into the mask interior.

* * * * *